United States Patent [19]

Kotzin et al.

[11] Patent Number: 5,776,708
[45] Date of Patent: Jul. 7, 1998

[54] METHOD FOR IDENTIFYING T CELLS INVOLVED IN AUTOIMMUNE DISEASE

[75] Inventors: Brian L. Kotzin; Philippa Marrack; John Kappler; Xavier Paliard. all of Denver, Colo.

[73] Assignee: National Jewish Center for Immunology and Respiratory Medicine, Denver, Colo.

[21] Appl. No.: 170,114

[22] Filed: Dec. 20, 1993

Related U.S. Application Data

[63] Continuation of Ser. No. 732,114, Jul. 18, 1991, Pat. No. 5,298,396, which is a continuation-in-part of Ser. No. 488,353, Mar. 2, 1990, abandoned, which is a continuation-in-part of Ser. No. 437,370, Nov. 15, 1989, Pat. No. 5,336,598.

[51] Int. Cl.$^6$ .......................... C12Q 1/68; G01N 33/564
[52] U.S. Cl. .......................... 435/7.24; 435/6; 436/501; 436/506; 436/509; 436/548
[58] Field of Search .............. 435/6, 7.24; 436/506, 436/509, 548, 501

[56] References Cited

U.S. PATENT DOCUMENTS

| | | |
|---|---|---|
| 4,677,061 | 6/1987 | Rose et al. |
| 4,683,195 | 7/1987 | Mullis et al. ............................ 435/6 |
| 4,886,743 | 12/1989 | Hood et al. ............................ 435/6 |
| 5,112,735 | 5/1992 | Albertini ............................ 435/6 |
| 5,223,426 | 6/1993 | Skibbens et al. ............... 435/240.27 |
| 5,336,598 | 8/1994 | Kotzin et al. ..................... 435/7.24 |
| 5,612,035 | 3/1997 | Howell et al. .................... 424/185.1 |

FOREIGN PATENT DOCUMENTS 9011294  10/1990  WIPO.

OTHER PUBLICATIONS

Abe and Hodes (1988) J. Immunol. 140:4132.
Babbitt et al. (1985) Nature 317:359.
Bekoff et al. (1987) J. Immunol. 139:3189.
Bill et al. (1989) J. Exp. Med. 169:1405.
Bjorkman et al. (1987) Nature 329:506.
Burmester et al. (1981) Arth. and Rheum. 24:1370.
Buus et al. (1987) Science 235:1353.
Choi et al. (1990) J. Exp. Med. 172:981.
Duqyesnoy et al. (1984) Hum. Immunol. 10:165.
Dyson et al. (1991) Nature 349:531.
Fox et al. (1982) J. Immunol. 128:351.
Gibofsky et al. (1978) J. Exp. Med. 148:1728.
Grey et al. (1989) Scientific American 261:56.
Hedrick et al. (1982) Cell 30:141.
Hemler et al. (1986) J. Clin. Invest. 78:696.
Herzog et al. (1987) The Lancet ii:1461.
Janeway et al. (1989) Immunol Rev. 107:61.
Kappler et al. (1988) Nature 332:35.
Kappler et al. (1987) Cell 49:273.
Kappler et al. (1989) Science 244:811.
Kappler et al (1987) Cell 49:263.
Karsh et al. (1979) Arth. and Rheum.22:1055.
Kotzin et al. (1981) New Engl. J. Med. 305:969.
Kronenberg (1986) Ann. Rev. Immunol. 4:529.
Legrand et al. (1984) Am. J. Hum. Genet. 36:690.
MacDonald et al. (1988) Nature 332:40.
Male et al. (1987) *Advanced Immunology* (J.B. Lippincott Company) chs. 6–10.
Marrack and Kappler (1990) Science 248:705.
Marrack et al. (1991) Nature 349:524.
Marrack and Kappler (1988) Immunol. Today 9:308.
Marrack and Kappler (1988) Nature 332:840.
McMichael et al. (1977) Arth. and Rheum. 20:1037.
Paulus et al. (1977) Arth. and Rheum. 20:1249.
Pullen et al. (1988) Nature 335:796.
Schiff et al. (1982) Ann. Rheum. Dis. 41:403.
Stamenkovic et al. (1988) Proc. Natl. Acad. Sci. USA 85:1179.
Townsend et al. (1986) Cell 44:959.
White et al. (1989) Cell 56:27.
Woodland et al. (1991) Nature 349:529.
Yocum et al. (1988) Ann. Int. Med. 109:863.
H. Acha–Orbea et al. *Cell, 54,* 263–273, 1988.
B. Kotzin et al. *Journ. Cellular Biochem., Suppl. 15,* (Part E), 144, 1991.
A. Sottini et al. *Europ. Journ. Immunol., 21,* 461–466, 1991.

*Primary Examiner*—David Saunders
*Attorney, Agent, or Firm*—Swanson & Bratschun, L.L.C.

[57] ABSTRACT

The invention relates to a method for identifying T cell populations involved in autoimmune diseases. This involves determining levels of a Vβ element in a body fluid sample of a patient and comparing this to normal levels. Variation from normal levels is indicative of an autoimmune disease. The invention also involves assaying T cell subpopulations in a sample to determine clonality of β chains. Clonality can also be used to diagnose autoimmune disorders.

22 Claims, 1 Drawing Sheet

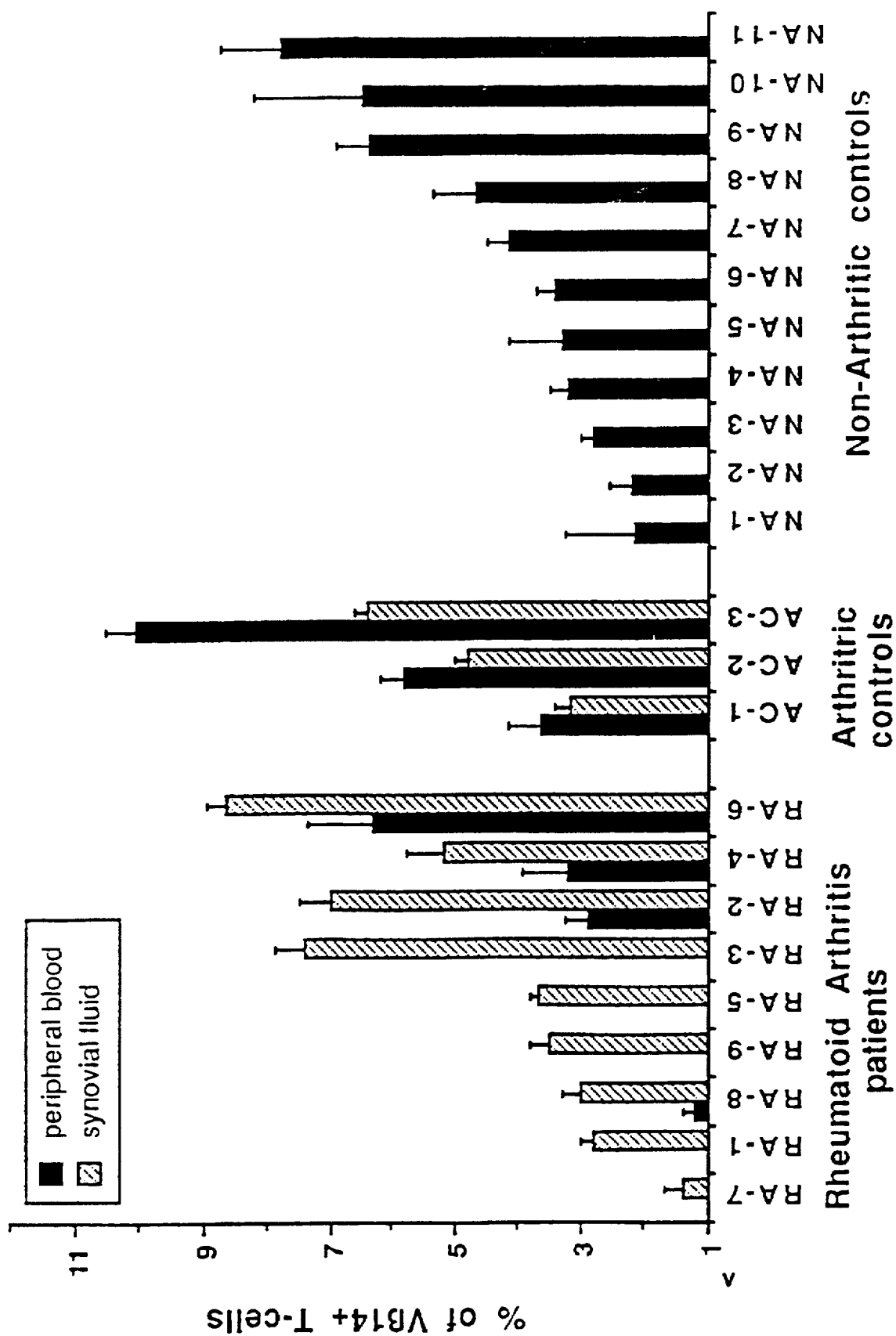

METHOD FOR IDENTIFYING T CELLS INVOLVED IN AUTOIMMUNE DISEASE

RELATED APPLICATIONS

This application is a continuation of Ser. No. 07/732,114 filed Jul. 18, 1991, now U.S. Pat. No. 5,298,396, which is a continuation-in-part of application Ser. No. 488,353 filed Mar. 2, 1990 now abandoned, which is itself a continuation-in-part of Ser. No. 437,370 filed Nov. 15, 1989, now U.S. Pat. No. 5,336,598.

FIELD OF THE INVENTION

This invention relates to methods for identifying T cell populations involved in autoimmune disorders, such as rheumatoid arthritis. More specifically, it relates to quantifying particular T cell subpopulations via assaying for specific Vβ elements. In addition, the invention relates to treatment of these conditions and disorders via administration of an agent which inhibits the particular T-cell subpopulation, identification of agents, such as superantigens and environmental factors involved in the development of autoimmune diseases, identification of subpopulations of T cell populations, and diagnosis of autoimmune diseases.

BACKGROUND AND PRIOR ART

In recent years, the mechanism by which mammalian immune systems, such as human and murine systems react to infections, foreign antigens, and to so-called "self antigens" in connection with autoimmune diseases has begun to be established. See, in this regard, Grey et al., Scientific American 261(5): 56–64 (1989); Male et al., *Advanced Immunology* (J. P. Lippincott Company, 1987), especially chapters 6 through 10.

Well known, both to the skilled artisan and to the general public is the role of antibodies, sometimes referred to as "immunoglobulin" or the less correct and older "gamma-globulin" in response to infection. Antibodies are protein molecules which are produced by B cells in response to infection. It is well known that these antibodies act to "disable" or to inactivate infectious agents in the course of combating the infection.

In order for antibodies to be produced, however, preceding events must occur which lead to stimulation of the B cells which produce the antibodies. One of the key events involved in the processes leading to antibody production is that of antigen recognition. This aspect of the immune response requires the participation of so-called "T-cells", and is less well known than the antibody response commented on supra.

Briefly, and in outline form, antigen recognition requires interaction of an "antigen presentation cell", a "processed antigen", and a T-cell. See Grey and Male, supra. The "processed antigen", in an infection, is a molecule characteristic of the pathogen which has been treated, i.e., "processed", by other cells which are a part of the immune system. The processed antigen interacts with a receptor on the surface of an antigen presented in a manner not unlike a lock fitting into a key hole or, perhaps more aptly, two pieces of a jigsaw puzzle.

The configuration of the complex processed antigen and receptor on antigen presentation cell allows the participation of T-cells. T-cells do not join the complex unless and until the processed antigen has fit into the receptor on the antigen presentation cell. This receptor will hereafter be referred to by its scientific name, the major histocompatibility complex (MHC), or the human leukocyte antigen (HLA). Generally, MHC is used to refer to murine systems, and HLA to humans.

These receptors fall into two classes. MHC-II molecules are involved in most responses to pathogens. In contrast, MHC-I molecules are involved when the pathogen is a virus, or a malignant cell is involved. When MHC-I participation is involved, there is no antibody stimulation; rather, the interaction of MHC-I, processed antigen and T-cell leads to lysis of cells infected with the pathogen.

The foregoing discussion has focused on the events involved in responding to "infection", i.e., the presence of pathogenic foreign material in the organism. Similar mechanisms are involved in autoimmune diseases as well. In these conditions, the organism treats its own molecules as foreign, or as "self-antigens". The same type of complexing occurs as described supra, with an antibody response being mounted against the organism itself. Among the diseases in which this is a factor are rheumatoid arthritis, diabetes, systemic lupus erythrematosis, and others.

The ability of the T-cell to complex with the processed antigen and MHC/HLA complex is dependent on what is referred to as the T-cell antigen receptor, referred to as "TCR" hereafter. The TCR is recognized as a heterodimer, made up of alpha ($\alpha$) and beta ($\beta$) chains. Five variable elements, coded for by germline DNA and known as V$\alpha$, J$\alpha$, V$\beta$, J$\beta$ and V$\beta$ as well as non-germline encoded amino acids contribute to the TCR. See, in this regard, Marrack et al., Immunol. Today 9: 308–315 (1988); Toyonaga et al., Ann. Rev. Immunol. 5: 585–620 (1987); Davis, Ann. Rev. Immunol. 4: 529–591 (1985); Hendrick et al., Cell 30: 141–152 (1982). With respect to the binding of TCR with processed antigen and MHC, see Babbitt et al., Nature 317: 359–361 (1985); Buus et al., Science 235: 1353–1358 (1987); Townsend et al., Cell 44: 959–968 (1986); Bjorkman et al., Nature 329: 506–512 (1987).

Generally, both the alpha and beta subunits are involved in recognition of the ligand formed by processed antigen and MHC/HLA molecule. This is not always the case, however, and it has been found that so-called "superantigens" stimulate T-cells with a particular V$\beta$ element, regardless of any other element. See Kappler et al., Cell 49: 273–280 (1987); Kappler et al., Cell 49: 263–271 (1987); MacDonald et al., Nature 332: 40–45 (1988); Pullen et al., Nature 335: 796–801 (1988); Kappler et al., Nature 332: 35–40 (1988); Abe et al., J. Immunol. 140: 4132–4138 (1988); White et al., Cell 56: 27–35 (1989); Janeway et al., Immunol. Rev. 107: 61–88 (1989); Berkoff et al., J. Immunol. 139: 3189–3194 (1988), and Kappler et al., Science 244: 811–813 (1989).

The "superantigens" mentioned supra, while generally stimulating T-cells as long as they possess a V$\beta$ element, are somewhat specific in terms of the particular form of the V$\beta$ moiety which is present on the stimulated T cell.

Rheumatoid arthritis ("RA") is an autoimmune disease characterized by chronic inflammation of multiple joints. Mononuclear cell infiltration of the synovial membrane can lead eventually to the destruction of articular cartilage and surrounding structures. Because of its high frequency and potentially severe nature, this disease is a major cause of chronic disability in adults. Although the pathogenesis of RA and other similar autoimmune diseases remains unknown, both genetic and environmental factors have been implicated. Several lines of evidence suggest that T cells specific for self-antigens may play a critical role in the initiation of these diseases. In the case of RA, the linkage of the disease to the DR4 and DR1 alleles of the Class II genes of the major histocompatibility complex (MHC) and the finding of sometimes oligoclonal, activated CD4+ T cells in synovial fluid and tissue of affected joints (Stastny et al., New Engl. J. Med. 298: 869 (1976); Gibofsky et al., J. Exp. Med. 148: 1728 (1978); McMichael et al., Arth. Rheum. 20: 1037 (1977); Schiff et al., Ann. Rheum. Dis. 41: 403 (1982); Duquesnoy et al., Hum. Immunol. 10: 165 (1984); Legrand et al., Am. J. Hum. Genet. 36: 690 (1984); Gregerse et al., Arth. Rheum. 30: 1205 (1987); Nepon et al., Arth. Rheum 32: 15 (1989); Burmester et al., Arth. Rheum. 24: 1370 (1981); Fox et al., J. Immunol. 128: 351 (1982); Hemler et al., J. Clin. Invest. 78: 696 (1986); Stamenkoic et al., Proc. Natl. Acad. Sci. U.S.A. 85: 1179 (1988) suggest the involvement of CD4+, $\alpha\beta$TCR-bearing, Class II-restricted T cells in the disease. This view is supported by the finding that partial elimination or inhibition of T cells by a variety of techniques can lead to an amelioration of disease in certain patients (Paulus et al., Arth. Rheum. 20: 1249 (1977); Karsh et al., Arth. Rheum. 22: 1055 (1979); Kotzin et al., N. Eng. J. Med. 30: 969 (1989); Trentham et al., N. Eng. J. Med. 305: 976 (1989); Herzog et al., Lancet ii: 1461 (1987); Yocum et al., Ann. Int. Med. 109: 863 (1989).

Usually, potentially autoreactive T cells are deleted or inactivated by encounter with self-antigen during their development, before they can damage the individual (Kappler et all, Cell 49: 273 (1987); Marrack et al., Nature 332: 840 (1988); Kappler et al., Nature 32: 35 (1988); MacDonald et al., Nature 332: 40 (1988); Pullen et al., Nature 35: 796 (1988); Bill et al., J. Exp. Med. 169: 1405 (1989); Kisielow et al., Nature 333: 742 (1988); Ramsdell et al. Science 246: 1038 (1989). In order to understand autoimmunity one must understand how self-reactive T cells escape these processes to become part of the mature T cell pool and what factors control whether these cells will remain quiescent or become activated to induce autoimmune disease. One suggested scenario has been that a self-antigen which is sequestered, at very low levels or presented on inappropriate cells may fail both to remove specific T cells during development and to activate these cells once they mature. Occasionally, however, microbial antigens cross-reactive with the self-antigens may lead to activation of these specific T cells. Once activated these cells may now recognize and chronically respond to the previously ignored self-antigen, leading to autoimmune disease. One difficulty with this suggestion is the low probability of a cross-reaction between two infrequently recognized antigens. However, recently a set of unusual microbial antigens, i.e., the superantigens have been identified (Kappler et al., supra; Marrack et al., supra; Kappler et al., Science 244: 811 (1989); Marrack et al., Science 248: 705 (1990); White et al., Cell 56: 27 (1989); Tomai et al., J. Exp. Med. 172: 359 (1990); Choi et al., J. Exp. Med. 172: 981 (190); Marrack et al., Nature 349: 524 (1991); Frankel et al., Nature 349: 526 (1991); Woodland et al., Nature 349: 529 (191); Dyson et al., Nature 349: 531 (1991). Because superantigens engage virtually all T cells whose TCR bears a particular V$\beta$ they can effect a much larger number of T cells than conventional antigenic peptides, which require target T cells to bear the correct versions of all the TCR variable elements (V$\alpha$, J$\alpha$, V$\beta$, D$\beta$, J$\beta$). Superantigens are, therefore, statistically more likely than conventional microbial antigens to crossreact with self-antigens and it has been suggested that they may play a role in induction of autoimmunity (Marrack et al., Science 248: 705 (1990).

It has now been found that T cells carrying specific V$\beta$ elements are associated with different pathological conditions. In Ser. No. 437,370 now U.S. Pat. No. 5,336,598, it was shown that infection by a superantigen presenting organism could be detected and diagnosed by assaying for particular V$\beta$ elements in a T cell containing sample. In Ser. No. 488,353 now abandoned, this phenomenon was shown to be true for toxic shock related disorders as well.

It has also been found that specific V$\beta$ elements can be associated with autoimmune disease, including rheumatoid arthritis. It has been found, quite surprisingly, that T cell populations and subpopulations are implicated and/or involved in autoimmune disorders, and it is possible to identify these and to correlate their presence to particular autoimmune diseases. This, in part, is the subject of the invention.

It has also been found that, within T cell containing samples, evidence of "clonality", a term which is explained infra, is also evidence of an autoimmune disorder. The invention, in general, thus relates to a method for assaying for V$\beta$ elements in T cell containing body fluid samples. The levels obtained are compared to levels in normal individuals, and variation from the normal is an indication of an autoimmune condition.

SUMMARY OF THE INVENTION

The invention provides for a method for determining a T cell sample implicated in an autoimmune disease, by assaying a T cell containing body fluid sample to determine level of a V$\beta$ element characteristic of the pertinent T cell population. The level thus determined is compared to levels in a comparable T cell containing body fluid sample, and the levels are compared. Variation from the normal level is indicative of the pathological condition.

Also provided by the invention is a method for determining a pathological condition by determining clonality of a particular subpopulation of a T cell sample in a body fluid sample. "Clonality", as used herein, relates to the relationship or lack thereof between nucleic acid sequence coding for the $\beta$ chain of the TCR.

In a preferred embodiment, the V$\beta$ elements are assayed via polymerase chain reaction ("PCR"), although it is also possible to determine these via other methods, such as with antibodies specific for the V$\beta$ element.

The invention will be explained in the disclosure which follows.

BRIEF DESCRIPTION OF THE FIGURE

FIG. 1 sets forth the distribution of T cells which display T cells showing V$\beta$14+ phenotype in patients with rheumatoid arthritis, as well as in patients with other forms of arthritis, and non-arthritic donors.

DETAILED DESCRIPTION OF PREFERRED EMBODIMENTS

EXAMPLE 1

In order to select subjects for the experiments which follow, patients from the rheumatology clinics of Fitzsimons Army Medical Center were chosen. Selection criteria included satisfaction of the criteria for classical or definite rheumatoid arthritis established by the American Rheumatism Association and the availability of synovial fluid from the subject. All patients had active inflammatory disease at the time that blood and synovial fluid samples were taken. The patients were classified via stage of disability and as to whether there were bone erosions and/or joint deformations found upon radiographic and physical examination. The classification "destructive" is used for these patients. "Stage 1" refers to ability to perform all usual activities without handicap. "Stage 2" refers to ability to carry out normal activity, but with pain. "Stage 3" refers to an inability to accomplish some normal activities, usual occupation or self care; and "Stage 4" refers to patients who are largely or totally incapacitated or bed ridden.

Subjects were also taking any of a variety of drugs at the time of sampling, including standard "NSAIDs" (non-steroid anti-inflammatory drugs); prednisone, gold compounds administered intramuscularly, d-penicillinamine, methotrexate, azathioprine, and hydroxychloroquine. Patients were assayed to determine if rheumatoid arthritis factor was present, and if so, the titer. Finally, patient samples were also assayed to determine human leukocyte antigen ("HLA") Class-II type.

These data are summarized in Table 1, which follows, together with data from arthritic controls (i.e., patients with non-rheumatoid arthritis), and non-arthritic controls.

All but one of the rheumatoid arthritis patients expressed HLA-DR4, which is not surprising as this allele has been associated with rheumatoid arthritis previously.

CD3 antibodies for three days, and were then cultured in the presence of interleukin-2 for 24 hours, following Kappler et al., Science 244: 811 (1989); Choi et al., J. Exp. Med. 172: 981 (1990), and Choi et al., Proc. Natl. Acad. Sci. U.S.A. 86: 8941 (1989). Total RNA was then isolated from these cells, following the above references. Great care was taken to prevent cross contamination, and none of the synovial fluid samples tested showed red blood cell contamination.

Two micrograms of total RNA were then used to synthesize first cDNA strains, using reverse transcriptase and random hexonucleotides, following art recognized techniques. This reaction was stopped by heating at 95° C., and the cDNA was then amplified via polymerase chain reaction (PCR) using a Vβ specific oligomer, an oligomer from downstream β chain constant region and two oligomers from the Cα region. These primers are described in Choi et al., J. Exp. Med. 172: 981 (1990), and Choi et al., Proc. Natl. Acad. Sci. 86: 8941 (1981), both of which are incorporated by reference as well as copending patent application Ser. No. 437,370 now U.S. Pat. No. 5,336,598 and Ser. No. 488,353 now abandoned, also incorporated by reference. Amount of cDNA and number of PCR cycles used were determined for each preparation to ensure that the amount of synthesis was

TABLE 1

|  | HLA-class II type | Age/disease duration (years) | Disease characterisitics | Rheumatoid factor liter | Medications |
|---|---|---|---|---|---|
| Rheumatoid Arthritis |  |  |  |  |  |
| RA-1 | ND | 3 1/2 | destructive, stage 2 | 1:320 | NSAID |
| RA-2 | -DR4, w12; -DRw52, w53; -DQw3 | 52/11 | destructive, stage 3 | 1:5120 | NSAID, Pred, d-Pen |
| RA-3 | -DR4; -DRw53; -DQw3 | 67/11 | nodular, destructive, stage 4 | 1:320 | NSAID |
| RA-4 | -DR4, w14;, -DRw53; -DQw1, w7 | 69/44 | nodular, destructive, stage 2 | 1:1280 | Pred |
| RA-5 | -DR1, 4; -DRw53; -DQw1, w3 | 64/6 | destructive, stage 2 | 1:5120 | NSAID, Pred, MTX |
| RA-6 | -DR1, w15; -DQw1 | 40/7 | destructive, stage 2 | Neg | NSAID, Pred, Gold |
| RA-7 | -DR4, w11; -DRw52, w53; -DQw3 | 50/7 | destructive, stage 2 | 1:640 | NSAID, Pred, Gold, HC |
| RA-8 | -DR1, 4; -DRw53; -DQw1, w3 | 69/8 | nodular, destructive, stage 3 | 1:1280 | NSAID, Pred, Aza |
| RA-9 | -DR3, 4: -DRw52, w53; - DQw2, 3 | 73/28 | nodular, destructive, stage 3 | 1:5120 | NSAID, d-Pen |
| Arthritic controls |  |  |  |  |  |
| AC-1 | -DR4, w11; -DRw52, w53; -DQw3 | 71/13 | Psoriatic arthritis, destructive, stage 3 | Neg | NSAID, MTX |
| AC-2 | ND; -B27⁻ | 23/<1 | Reiter's syndrome 2° chlamydia; arthritis, conjunctivitis, urethritis, balanitis, stage 2 | Neg | NSAID |
| AC-3 | ND; -B27⁺ | 28/<1 | Reiter's syndrome 2° salmonella enteriditis; arthritis, diarrhea, conjuctivitis, urethritis, stage 2 | Neg | NSAID |
| Non-Arthritic controls |  |  |  |  |  |
| NA-1 | -DR-4, w11; -DRw52, w53; -DQw7 |  |  |  |  |
| NA-2 | -DR2, w11; -DRw52, w53; -DQw3, w6 |  |  |  |  |
| NA-3 | -DR1; -DQ5 |  |  |  |  |
| NA-4 | -DR3, 4; -DRw52, w53, -DQ2, 7 |  |  |  |  |
| NA-5 | -DR3, 4; -DRw52, w53; -DQw2, w3 |  |  |  |  |
| NA-6 | ND |  |  |  |  |
| NA-7 | -DR4; -DRw53; -DQw7 |  |  |  |  |
| NA-8 | -DR2, 4; -DQw1, w3 |  |  |  |  |
| NA-9 | -DR1, 4; -DQw1, w3 |  |  |  |  |
| NA-10 | -DR4, 4 |  |  |  |  |
| NA-11 | -DR4, 4 |  |  |  |  |

EXAMPLE 2

Studies were undertaken to determine TCR-Vβ presence and usage by individuals with rheumatoid arthritis. To do so, samples of mononuclear cells from peripheral blood and synovial fluid were isolated via Ficoll-Hypaque density gradient centrifugation. The cells were stimulated with antiproportional to the amount of Vβ mRNA in the original sample. The amplified products were quantified using $^{32}$P end labeled 3' primers (~5×10$^5$ cpm each), and were analyzed after separation of products on a 2% agarose gel. Percentages of T cells bearing each Vβ element were obtained by normalizing cpms in Vβ band to that in the Cα band, which serves as internal control, and then transforming into a calculated percentage using a standard curve as per Choi et al., Proc. Natl. Acad. Sci. U.S.A. 86: 8941 (1981).

The Vβ determinations were repeated at least twice, and usually four times. For several patient samples, i.e., those from RA-1, 3, 5 and 6, increasing numbers of cycles were carried out using Vβ14 and control Vβ2 specific primers to ensure that differences in percentages of Vβ14 bearing cells were reproducible and that primer efficiencies were comparable. The results are presented in Table 2 as percentages±standard deviation where PBL refers to peripheral blood lymphocytes and Sfld refers to synovial fluid.

To summarize these data, about 10% of PBLS bear Vβ2, and from 4–13% bear Vβ13.1, while less than 2% show Vβ20. Differential expression is thus present. Some Vβ expression varies from patient to patient. For example, Vβ12 was found on less than 1% of PBL T cells in patients RA-2 and 5, but up to 7% in others. These variations were conserved from test to test and over time.

While synovial fluid TCR Vβ repertoire tended to mirror the findings in PBLS, there were some "mismatches". Note, e.g., the higher percentages of Vβ12, 13.1, 14 and 15 in the synovial fluid of patient RA-5 as compared to peripheral blood, while Vβ 5.1, 8 and 10 exhibited the converse. This indicates that infiltration of synovial fluid by T cells in rheumatoid arthritis is not totally random or passive.

A key finding was the higher percentage of Vβ14$^+$ T cells in the synovial fluid of all seven patients as compared to the peripheral blood. This was due to strikingly low levels of Vβ14$^+$ T cells in the blood. The only time such a skewing did not occur was in patient RA-6, who was DR4$^-$ and did not show rheumatoid factor.

When two other individuals were studied in the same manner (RA8 and 9 of FIG. 1), the same skewing was found. The difference between the levels was highly significant using student's test analysis

TABLE 2

| Vβ | RA-1 PBL | RA-1 Sfld | RA-2 PBL | RA-2 Sfld | RA-3 PBL | RA-4 Sfld | RA-4 PBL | RA-4 Sfld |
|---|---|---|---|---|---|---|---|---|
| 1 | 5.52 (0.76) | 6.58 (0.44) | 3.32 (0.40) | 4.62 (0.51) | 2.77 (0.23) | 2.97 (0.23) | 3.71 (0.73) | 4.44 (0.42) |
| 2 | 10.27 (1.11) | 6.92 (0.51) | 7.08 (0.42) | 6.87 (1.02) | 8.44 (0.72) | 2.53 (0.31) | 10.57 (1.33) | 10.90 (0.43) |
| 3 | 8.91 (0.45) | 6.33 (0.20) | 9.97 (0.47) | 11.29 (0.61) | 17.55 (2.59) | 5.17 (0.05) | 15.01 (2.56) | 17.65 (3.24) |
| 4 | 2.36 (0.32) | 1.70 (0.04) | 1.52 (0.69) | 1.21 (0.32) | 3.20 (0.32) | 2.97 (0.19) | <1 | 1.89 (0.36) |
| 5.1 | 3.57 (0.56) | 1.78 (0.17) | 2.35 (0.12) | 2.51 (0.11) | 3.65 (0.53) | 2.78 (0.30) | 2.25 (0.79) | 1.74 (0.32) |
| 5.2–3 | 2.63 (0.09) | <1 | 3.36 (0.80) | 4.58 (0.06) | 3.15 (0.21) | 5.12 (0.27) | 4.22 (0.36) | 3.66 (0.20) |
| 6.1–3 | 6.74 (0.35) | 5.62 (0.04) | 8.01 (0.92) | 5.21 (0.66) | 11.47 (1.17) | 13.94 (1.77) | 4.93 (0.78) | 8.30 (0.65) |
| 7 | 11.49 (1.37) | 5.09 (1.03) | 6.49 (0.41) | 4.44 (0.22) | 2.45 (0.13) | 6.07 (0.94) | 2.52 (1.12) | 5.83 (0.03) |
| 8 | 5.53 (0.86) | 2.45 (0.33) | 3.92 (0.43) | 2.01 (0.11) | 4.62 (0.52) | <1 | 3.37 (0.14) | 6.58 (1.03) |
| 9 | <1 | 2.42 (0.19) | 1.09 (0.48) | <1 | 4.74 (0.37) | 2.59 (0.56) | <1 | 1.35 (0.47) |
| 10 | <1 | <1 | <1 | <1 | 1.04 (0.11) | <1 | 1.68 (0.53) | 1.07 (0.68) |
| 11 | 1.37 (0.07) | <1 | 1.10 (0.46) | 2.14 (0.38) | <1 | 1.38 (0.15) | 1.83 (0.22) | 2.02 (0) |
| 12 | 2.66 (0.16) | 1.30 (0.28) | <1 | <1 | 7.13 (0.96) | 2.83 (0.42) | 1.41 (0.17) | 4.34 (0.57) |
| 13.1 | 8.79 (0.63) | 6.43 (0.67) | 4.36 (0.12) | 2.82 (0.80) | 4.78 (0.07) | 9.98 (0.05) | 4.62 (0.38) | 6.25 (0.85) |
| 13.2 | 6.05 (0.59) | 4.72 (0.13) | 4.96 (0.16) | 4.67 (0.37) | 3.00 (0.31) | 13.54 (0.91) | 4.68 (0.62) | 1.58 (0.20) |
| 14 | <1 | 2.77 (0.21) | 2.85 (0.42) | 6.97 (0.54) | <1 | 7.42 (0.46) | 3.20 (0.71) | 5.16 (0.60) |
| 15 | 1.15 (0.12) | 1.18 (0.06) | 1.07 (0.18) | 1.87 (0.19) | 1.69 (0.42) | <1 | 2.00 (0.14) | <1 |
| 16 | 2.25 (0.27) | <1 | 1.04 (0.28) | 1.52 (0.25) | 2.45 (0.06) | 1.53 (0.02) | 2.87 (0.22) | 1.39 (0.43) |
| 17 | 3.75 (0.03) | 3.00 (0.36) | 3.30 (0.32) | 2.55 (0) | 2.10 (0.86) | 1.00 (0.21) | 4.66 (0.22) | 3.19 (0.18) |
| 18 | 1.38 (0.32) | <1 | 2.06 (0.22) | <1 | 2.50 (0.21) | 2.32 (0.18) | 1.39 (0.03) | 2.47 (0.46) |
| 19 | <1 | <1 | <1 | 1.41 (0.02) | 3.90 (0.42) | <1 | <1 | <1 |
| 20 | <1 | <1 | 1.65 (0.26) | 1.60 (0.21) | 3.60 (0.03) | <1 | <1 | <1 |
| Total Vβ | 85.4 | 63.2 | 73.6 | 71.3 | 92.8 | 86.3 | 76.7 | 90.8 |

| Vβ | RA-5 PBL | RA-5 Sfld | RA-6 PBL | RA-6 Sfld | RA-7 PBL | RA-7 Sfld |
|---|---|---|---|---|---|---|
| 1 | 5.78 (0.61) | 4.63 (0.47) | 5.53 (0.52) | 3.28 (0.14) | 7.22 (0.97) | 3.82 (0.35) |
| 2 | 13.63 (2.09) | 10.48 (0.76) | 13.35 (2.12) | 12.22 (1.52) | 11.79 (2.07) | 8.79 (1.76) |
| 3 | 9.74 (1.35) | 7.64 (0.28) | 7.91 (0.70) | 7.94 (1.03) | 3.00 (1.36) | 2.75 (0.40) |
| 4 | 2.11 (0.58) | <1 | 5.08 (0.57) | 3.28 (0.17) | <1 | <1 |
| 5.1 | 4.67 (0.23) | 2.62 (0.12) | 2.36 (0.14) | 1.33 (0.11) | 3.28 (0.19) | 1.65 (0.28) |
| 5.2–3 | 2.27 (0.03) | 2.63 (0.91) | 4.02 (0.65) | 1.51 (0.23) | 5.63 (0.99) | 1.51 (0.11) |
| 6.1–3 | 3.77 (0.123) | 5.58 (0.08) | 4.95 (0.27) | 5.61 (0.09) | 7.03 (0.47) | 4.27 (0.49) |
| 7 | 3.21 (0.80) | 3.07 (0.26) | 6.32 (0.86) | 4.82 (0.56) | 5.91 (1.31) | 6.87 (0.01) |
| 8 | 10.66 (0.20) | 3.53 (0.66) | 11.61 (1.47) | 2.09 (0.39) | 6.93 (0.95) | 3.27 (0.12) |
| 9 | <1 | <1 | <1 | <1 | <1 | <1 |
| 10 | 3.05 (0.64) | <1 | 1.25 (0.12) | <1 | <1 | <1 |
| 11 | 1.30 (0.12) | <1 | 2.45 (0.26) | <1 | <1 | <1 |
| 12 | <1 | 2.24 (0.13) | 3.74 (0.08) | <1 | 2.04 (0.07) | <1 |
| 13.1 | 3.74 (0.47) | 8.10 (1.36) | 12.09 (0.83) | 6.81 (0.23) | 10.89 (1.73) | 5.55 (1.98) |
| 13.2 | 2.60 (1.01) | 1.95 (0) | 2.60 (0.88) | 1.04 (0.10) | 1.39 (0.33) | 4.84 (0.09) |
| 14 | <1 | 3.69 (0.10) | 6.29 (1.09) | 8.65 (0.31) | <1 | 1.40 (0.29) |
| 15 | <1 | 2.36 (0.62) | 1.04 (0.06) | <1 | 1.36 (0.37) | <1 |
| 16 | 1.85 (0.17) | 1.90 (0.52) | <1 | <1 | <1 | <1 |
| 17 | 1.06 (0.07) | 1.25 (0.24) | 1.97 (0.03) | 1.72 (0.15) | 2.40 (0.37) | <1 |
| 18 | <1 | 1.45 (0.23) | <1 | <1 | <1 | <1 |
| 19 | 1.51 (0.45) | 1.26 (0.19) | <1 | <1 | <1 | <1 |
| 20 | 1.91 (0.59) | 2.67 (0.09) | <1 | <1 | <1 | <1 |
| Total Vβ | 76.0 | 68.3 | 93.2 | 64.9 | 74.5 | 51.9 |

EXAMPLE 3

The results set forth in Example 2 become more striking compared to experiments when patients with non-rheumatoid arthropathies were examined. Three patients (AC-1, 2 and 3 of Table 1), were subjected to the same sort of analysis carried out on the RA patients in Example 2. The results are presented in Table 3, which follows. The Vβ pattern was heterogeneous, with synovial fluid distribution similar to that found in PBL. Most importantly, no enrichment of Vβ14+ in synovial fluid was found.

Admittedly, patient RA-6 showed high levels of Vβ14+ in peripheral blood, but as has been pointed out, supra, patient RA-6 showed significant differences from other rheumatoid patients. These results show that the observed phenomenon of low level Vβ14+ presence in peripheral blood is attributable to rheumatoid arthritis, not expression of HLA-DR4.

EXAMPLE 5

Studies were carried out to determine if the Vβ14+ T cells found in the synovial fluid of rheumatoid arthritis patients

TABLE 3

| Vβ | AC-1 PBL | AC-1 Sfld | AC2 PBL | AC-2 Sfld | AC-3 PBL | AC3 Sfld |
|---|---|---|---|---|---|---|
| 1 | 5.21 (0.9) | 4.63 (0.17) | 2.53 (0.35) | 4.29 (0.57) | 4.23 (0.69) | 5.47 (0.54) |
| 2 | 8.42 (0.75) | 7.44 (0.06) | 5.27 (0.79) | 7.05 (0.74) | 8.06 (1.20) | 0.79 (0.44) |
| 3 | 12.11 (0.64) | 11.96 (0.55) | 9.81 (1.13) | 13.77 (1.73) | 8.63 (0.78) | 2.78 (0.11) |
| 4 | 2.03 (0.09) | 2.99 (0.28) | <1 | 2.21 (0.78) | <1 | <1 |
| 5.1 | 1.72 (0.11) | 1.63 (0.45) | <1 | <1 | 2.06 (0.23) | <1 |
| 5.2–3 | 4.77 (0.05) | 2.98 (0.12) | 3.79 (0.18) | 2.67 (0.77) | 2.07 (0.28) | 2.47 (0.54) |
| 6.1–3 | 6.53 (0.47) | 11.83 (0.89) | 10.34 (1.20) | 8.09 (0.39) | <1 | <1 |
| 7 | 6.34 (1.14) | 8.57 (0.91) | 10.87 (0.93) | 4.68 (0.63) | 4.49 (0.01) | 4.58 (0.69) |
| 8 | 4.24 (0.02) | 3.61 (0.06) | 4.15 (1.02) | 3.87 (0.30) | 1.01 (0.30) | <1 |
| 9 | <1 | 1.06 (0.10) | 1.92 (0.07) | 1.74 (0.45) | 3.00 (0.33) | 4.30 (0.58) |
| 10 | 1.02 (0.31) | <1 | 1.40 (0.16) | <1 | <1 | <1 |
| 11 | 1.87 (0.18) | 1.95 (0.17) | 1.03 (0.25) | 1.35 (0.06) | 1.43 (0.17) | 1.45 (0.15) |
| 12 | 1.53 (0.31) | 1.86 (0.40) | 1.32 (0.38) | 2.43 (0.74) | 1.32 (0.85) | 2.89 (0.24) |
| 13.1 | 4.76 (0.44) | 5.17 (0.81) | 8.72 (0.94) | 5.63 (0.32) | 7.01 (1.05) | 5.02 (0.36) |
| 13.2 | 3.31 (0.16) | 2.06 (0.04) | 2.38 (0.54) | 2.23 (0.27) | 5.58 (0.23) | 3.81 (0.45) |
| 14 | 3.65 (0.5) | 3.17 (0.27) | 5.80 (0.38) | 4.79 (0.21) | 10.04 (0.48) | 6.38 (0.22) |
| 15 | 1.26 (0.34) | 2.08 (0.06) | 1.27 (0.05) | 1.02 (0.06) | 5.08 (0.36) | 2.83 (1.01) |
| 16 | <1 | <1 | 1.12 (0.31) | <1 | 1.87 (0.08) | 2.12 (0.26) |
| 17 | 3.50 (0.03) | 2.83 (0.27) | 4.18 (0.02) | 2.97 (0.25) | <1 | <1 |
| 18 | 1.01 (0.48) | <1 | <1 | <1 | <1 | <1 |
| 19 | 1.47 (0.10) | 1.54 (0.37) | <1 | <1 | <1 | <1 |
| 20 | 1.48 (0.08) | 1.02 (0.14) | <1 | <1 | <1 | <1 |
| total Vβ | 77.4 | 79.8 | 79.2 | 73.0 | 70.9 | 60.7 |

EXAMPLE 4

Following the unexpected finding of the low levels of Vβ14+ T cells in the peripheral blood of rheumatoid arthritis patients, experiments were carried out to determine if this phenomenon was associated with rheumatoid arthritis rather than HLA or MHC II subtype. To do this, the same type of assay was carried out, using PCR, on 9 rheumatoid arthritis patients, three arthritic controls, and eleven non-arthritic controls. Many of the non-arthritic patients also expressed HLA-DR4 MHC II subtype, as shown in Table 1 (i.e., "NA 1, 4, 5, and 7–10). Five "RA" patients had less than 1% Vβ14+ T cells in peripheral blood. In contrast, the lowest level in normal patients was 2% and it ranged up to 6%.

were oligoclonal. To do this, PCR generated β chain fragments were cloned into an EcoRI-BamHI cut version of plasmid pTZ18R. Double stranded plasmid DNAs were prepared with acid phenol, following Weichert et al., in Editorial Comments (Cleveland: U.S. Biochemical Corp., 1989), page 5. A Sequanase kit was then used to directly sequence these β chains. As controls, Vβ 13.2, which is closely related to Vβ14, and Vβ2 which is quite distantly related to Vβ14 (Siu et al., J. Exp. Med. 164: 1600 (1986)) were used. For the comparison, Vβ14+ cDNA clones from peripheral blood of one "RA" patient and one "NA" patient were sequenced, as well as one from synovial fluid of an "AC" patient.

TABLE 4

Analysis of β chain sequences from synovial fluid and peripheral blood T cells

| Patient | Tissue | Vβ | No. of Sequences | No. of Occur. | % of Total | Juctional Sequence Vβ-NDβN-Jβ | No. | % of Total | Jβ1 1 2 3 4 5 6 | Jβ2 1 2 3 4 5 6 7 |
|---|---|---|---|---|---|---|---|---|---|---|
| RA-2 | Synovial Fluid | 14 | 18 | 11 | 61 | CASSL—SRP—DTQY(Jβ2.3) (SEQ ID NO:1) | 5 | 28 | 0 0 1 0 0 1 | 1 0 2 0 0 0 0 |
|  |  |  |  | 2 | 11 | CASSL—YGTYN—TQY(Jβ2.3) (SEQ ID NO:2) |  |  |  |  |
|  |  | 13.2 | 18 | 2 | 11 | CAS—KRVSD—NEQF(Jβ2.1) (SEQ ID NO:3) | 14 | 78 | 1 0 0 0 1 1 | 5 1 1 1 1 0 2 |
|  |  |  |  | 2 | 11 | CAS—MGLAG—QETQY(Jβ2.5) (SEQ ID NO:4) |  |  |  |  |
|  |  | 2 | 18 | 3 | 17 | CSA—IDRA—SYEQY(Jβ2.7) (SEQ ID NO:5) | 15 | 83 | 0 0 0 1 1 0 | 5 0 3 1 0 0 4 |
|  | Peripheral Blood | 14 | 18 | 0 | 0 |  | 18* | 100 | 0 1 0 0 1 1 | 5 0 3 1 0 0 4 |

TABLE 4-continued

Analysis of β chain sequences from synovial fluid and peripheral blood T cells

| | | | | | Sequence Occurring More Than Once | | Sequence Occuring Once | | |
|---|---|---|---|---|---|---|---|---|---|
| Pa-tient | Tissue | Vβ | No. of Sequences | No. of Occur. | % of Total | Juctional Sequence Vβ-NDβN-Jβ | No. | % of Total | Jβ1 Jβ2<br>1 2 3 4 5 6 1 2 3 4 5 6 7 |
| RA-1 | Synovial Fluid | 14 | 21 | 13 | 62 | CASS—TG—NTEAF(Jβ1.1) (SEQ ID NO:6) | 6 | 29 | 0 0 0 0 1 0 0 0 3 0 0 1 1 |
| | | | | 2 | 10 | CAS—RLAS—NEQF(Jβ2.1) (SEQ ID NO:7) | | | |
| | | 13.2 | 17 | 7 | 41 | CASSL—VTSG—YNEQF(Jβ2.1) (SEQ ID NO:8) | 8 | 47 | 0 2 0 0 1 0 4 0 0 0 1 0 0 |
| | | | | 2 | 12 | CASS—YPTAG—NQPQH(Jβ1.5) (SEQ ID NO:9) | | | |
| RA-5 | Synovial Fluid | 14 | 22 | 7 | 32 | CAS—NPGGV—NTEAF(Jβ1.1) (SEQ ID NO:10) | 12 | 54 | 3 1 0 0 0 0 4 0 1 0 1 0 2 |
| | | | | 3 | 14 | CASS—PRGAY—TQY(Jβ2.3) (SEQ ID NO:11) | | | |
| AC-3 | Synovial Fluid | 14 | 17 | 3 | 18 | CAS—RSDRVG—NYGYT(Jβ1.2) (SEQ ID NO:12) | 9 | 53 | 0 1 0 0 0 0 2 1 1 0 3 0 1 |
| | | | | 3 | 18 | CA—NLRAA—TNEKLF(Jμ1.4) (SEQ ID NO:13) | | | |
| | | | | 2 | 12 | CASS—GRGDD—NQPQH(Jβ1.5) (SEQ ID NO:14) | | | |
| NC-7 | Perpherial Blood | 14 | 17 | 0 | 0 | | 17 | 100 | 1 2 0 0 2 0 5 2 2 0 0 0 3 |

*Although all clones sequenced from the PBL of this patient were unique, one was identical to the most frequent Vβ14 clone found in synovial fluid.

Table 4, infra shows these results. In brief, a few clones dominate the Vβ14⁺ T cell population of RA patients. Each patient showed that two clones accounted for 46–72% of the appropriate T cells. Dominant clonotypes were different in each patient, although restricted Jβ usage was observed. Nearly all Vβ14⁺ dominant clones used Jβ1.1 or Jβ2.3, while these clones accounted for only 39% of other RA synovial fluid Vβ14⁺ clones, and only 14% of peripheral blood Vβ14⁺ clones.

The Vβ14⁺ β chains from peripheral blood cells of RA and normal patients showed no evidence of clonality (none of 35 examined sequences were repeated). Thus, dominant clones do not represent an artifact of PCR amplification.

While there is some evidence for dominant T cell clones bearing other Vβs in synovial fluid, results are less dramatic than those seen with Vβ14. For example, when patient RA-1 is studied, 7 of 17 sequences which included Vβ13.2 had the same functional sequence, and three of 18 Vβ2 clones from patient RA-2 were identical.

These data support the idea that synovial fluid T cells, taken from patients with arthropathies, are made up of a collection of expanded clones, presumably with some specificity for the disease, as well as a large number of non-specifically recruited cells. For RA patients, the Vβ14 cells are particularly clonal, clearly suggesting a specific role for this T cell subtype in rheumatoid arthritis.

The foregoing data clearly show that it is possible to identify a T cell population which is implicated in an autoimmune disease by assaying for a Vβ element characteristic of the T cell population involved, and comparing it to a normal sample. It will be understood that "population" as used herein refers to T cells which express a particular Vβ element. T cells of a "Vβ14" population, e.g., may express certain other antigens on their surface, but they will all express Vβ14.

"Implicated" as used herein means that the T cell population is involved, either in whole or in part, with the development of the autoimmune condition. There may be other factors involved in a particular autoimmune pathology besides T cells, but T cells are always present.

In assaying the subject or patient, it is preferred to assay a T-cell containing body fluid sample because this is easier, but tissue samples can also be assayed, because T cells are found in tissues of patients with autoimmune disorders. "T-cell containing sample" therefore refers to any body fluid or tissue taken from the patient.

In the case of rheumatoid arthritis, the T cell population of relevance is Vβ14, and the examples show how this population of cells was identified. In these examples, synovial fluid and blood were assayed. Synovial fluid was selected because this is found at the site of deterioration associated with rheumatoid arthritis. It will be understood that for different autoimmune disorders exhibiting different pathologies, different fluids or tissues will be examined. Non-limiting examples include systemic lupus erythematosis, a multisystem disease, which admits of examination of blood, skin, joints, arteries, muscle, pericardium and glomeruli tissues and fluids. Similarly, Hashimoto's thyroiditis, a disease involving thyroid inflammation calls for assay of thyroid tissue and fluid, whereas Addison's disease would call for analysis of adrenal samples. Multiple sclerosis suggests study of nerve tissue, spinal fluid, brain tissue and cerebral fluid, while autoimmune diabetes mellitus suggests analysis of pancreatic samples or islet of Langerhans samples.

The assaying of Vβ elements has been exemplified by use of the polymerase chain reaction. This should not be considered to be the only way in which the Vβ element of interest can be determined. The art is aware of antibodies, including monoclonal antibodies which specifically bind to and thereby identify individual Vβ elements, e.g. Also, all methods for identifying or isolating particular proteins and peptides in a sample may be applied to the identification and quantification of Vβ elements. These are well known to the skilled artisan, and need not be repeated here.

The identification of a particular Vβ cell population with an autoimmune disease suggests a therapeutic method for treating the disease in question. It is known that, in autoimmune diseases T cells are involved in provoking and mediating immune responses. The identification of a specific Vβ cell type as associated with an autoimmune disease means that the disease can be treated by administering an agent which specifically inhibits or leads to inhibition of the cell type in question. An example of such an agent is an antibody or monoclonal antibody, but others are possible. For example, one can mount an immune response against the T cell population itself by administering a sample of the Vβ peptide with concomitant immune response. The immune response leads to identification, engagement and deletion of the T cell population causing the autoimmune disorder. This can also be done via administration of a so-called "superantigen", which engages the Vβ element and leads to deletion of the cell presenting it. In some cases, this may be done, preferably, by administering the agent directly to the site of the disorder, so that the response can be localized and controlled. For rheumatoid arthritis, e.g., one may administer an anti-Vβ14 antibody via injection at the site of joint deterioration.

One of the consequences of the data and experiments described herein is the ability to identify an agent associated with a particular autoimmune disease. It is known that a T cell response can be generated upon exposure of a mixed cell sample in vitro to an agent, and that a T cell response can be generated in an experimental animal. The invention permits one to identify a particular Vβ element carrying T cell sample as being associated with an immune disorder. Once this is accomplished, various suspected agents can be tested to see if they provoke the same response or a parallel response either in vitro or in vivo. "Parallel response" refers to a situation where an experimental animal, such as a mouse, is used to test the agent. The murine T cell repertoire parallels the human system, but they are not identical. One would look for a response typical of murine arthritis, e.g., when studying the causative agent for rheumatoid arthritis in humans.

"Agent" as used herein refers to any material which provokes a T cell response. Superantigens have been described supra, and are included within this definition, as are environmental factors including various carcinogens and other chemicals, naturally occurring substances, bacterial pathogens and endotoxins, and so forth.

Another consequence of the invention is the ability to identify even more restricted populations of T cells via assaying for clonality. To elaborate, whereas a population of T-cells may all contain the same Vβ element, this is only part of the β chain of the T cell receptor. The data supra indicate that within the T cell population found in a sample, while there is variation, certain β chains were predominant, clearly indicating that there was some process of selection leading to favoring of a particular T cell clone or clones. Where about 30% or more of a T cell population in a sample show identical β chains, this is evidence of clonality, and of autoimmune pathology. "Identical" as used herein has the meaning ascribed thereto by those skilled in the art, and can include some minor variation as permitted within a clonal population.

It will also be clear that this invention includes a method for diagnosing an autoimmune disorder where this is necessary or desirable. Again, this involves identifying T cell populations by assaying samples containing T cells and comparing values obtained for a Vβ element to normal values. Variation therefrom is indicative of an autoimmune disorder.

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

We claim:

1. A method for identifying a T-cell population implicated in an autoimmune disease, comprising:

(i) assaying a T-cell containing sample of a patient taken from a site characterized by deterioration thereof associated with said autoimmune disease to determine the expression of a particular Vβ element; and (ii) comparing said Vβ element expression with Vβ element expression from a comparable T-cell containing sample of a non-deteriorated body fluid or tissue from said patient, wherein variation therefrom is indicative of a T-cell population involved in said autoimmune disease.

2. The method of claim 1, wherein said T cell containing sample at the site of deterioration is a body fluid.

3. The method of claim 2, wherein said body fluid is blood.

4. The method of claim 1, wherein said T cell containing sample at the site of deterioration is a tissue.

5. The method of claim 1, comprising assaying said T cell containing samples by contacting the samples with an antibody which specifically binds to said Vβ element.

6. The method of claim 5, wherein said antibody is a monoclonal antibody.

7. The method of claim 1, comprising assaying said T cell containing samples by determining a level of expression of a DNA sequence which codes for and expresses said Vβ element.

8. The method of claim 7, comprising determining the level of expression via polymerase chain reaction.

9. The method of claim 1 wherein said variation is a difference in percentage of T cells expressing said Vβ element or the presence of clonality in the Vβ element expression of T cells at the site of deterioration.

10. A method for diagnosing an autoimmune disease comprising:
   (i) assaying a T-cell-containing body fluid or tissue sample taken from a site characterized by immune deterioration in a patient to determine expression of a particular Vβ element associated with said autoimmune disease, and
   (ii) comparing the expression of said Vβ element from the deteriorated site to the expression of said Vβ element in a non-deteriorated body fluid or tissue sample from said patient, wherein differences in the Vβ expression are indicative of said autoimmune disease.

11. The method of claim 10, wherein said autoimmune disease is rheumatoid arthritis.

12. The method of claim 10, wherein the T cell containing body fluid sample obtained from the site of non-deterioration is peripheral blood.

13. The method of claim 10, wherein said T cell containing body fluid sample obtained from the site of deterioration is synovial fluid.

14. The method of claim 10, wherein said Vβ element is Vβ14.

15. The method of claim 10, comprising assaying said T-cell containing body fluid sample taken from a site characterized by immune deterioration by determining the level of expression of a DNA sequence which codes for and expresses said Vβ element.

16. The method of claim 10, comprising assaying said T-cell containing body fluid samples by polymerase chain reaction.

17. The method of claim 10, comprising assaying said T-cell containing body fluid samples by contacting the samples with antibodies which specifically bind to said Vβ element.

18. The method of claim 17, wherein said antibodies are monoclonal antibodies.

19. A method for identifying a T-cell population implicated in an autoimmune disease, comprising:
   (i) assaying a T-cell containing sample of a patient taken from a site characterized by deterioration thereof associated with said autoimmune disease to determine the expression of a particular Vβ element; and
   (ii) comparing said Vβ element expression with Vβ element expression from a comparable T-cell containing sample from a non-deteriorated site from said patient wherein variation in the percentage of T cells expressing said Vβ element or the presence of clonality of the Vβ expressing population is indicative of a T-cell population involved in said autoimmune disease.

20. A method for determining clonality in a T-cell Vβ population implicated in an autoimmune disease, comprising:
   (i) assaying a sample from a site of deterioration in a patient, said sample having an amplified Vβ population implicated in the autoimmune disease to determine the number of different β sequences expressed therein, wherein each β sequence represents a different subpopulation; and
   (ii) determining the percentage of the Vβ population corresponding to each of the different β sequences, wherein clonality is indicated by one β sequence being present in a percentage greater than the percentage of said one β sequence in a non-deteriorated site in said patient.

21. The method of claim 20, wherein the different β sequences differ in their Jβ sequences.

22. A method of implicating a T cell subpopulation in an autoimmune disease, comprising the steps of:
   (i) assaying a Vβ population that is amplified at a site of deterioration in a patient to determine the number of different β sequences expressed therein, wherein each β sequence represents a different subpopulation; and
   (ii) determining the percentage of the Vβ population corresponding to each of the different β, sequences, wherein a T-cell subpopulation is implicated in an autoimmune disease when one β sequence is present in a percentage greater than the percentage of said one β sequence in a non-deteriorated site from said patient.

* * * * *

SEQUENCE LISTING ( 1 ) GENERAL INFORMATION:

( i i i ) NUMBER OF SEQUENCES: 14

( 2 ) INFORMATION FOR SEQ ID NO:1:

( i ) SEQUENCE CHARACTERISTICS:
        ( A ) LENGTH: 12 amino acids
        ( B ) TYPE: amino acid
        ( D ) TOPOLOGY: linear ( x i ) SEQUENCE DESCRIPTION: SEQ ID NO:1:

```
Cys  Ala  Ser  Ser  Leu  Ser  Arg  Pro  Asp  Thr  Gln  Tyr
               5                              10
```

( 2 ) INFORMATION FOR SEQ ID NO:2:

( i ) SEQUENCE CHARACTERISTICS:
        ( A ) LENGTH: 13 amino acids
        ( B ) TYPE: amino acid
        ( D ) TOPOLOGY: linear ( x i ) SEQUENCE DESCRIPTION: SEQ ID NO:2:

```
Cys  Ala  Ser  Ser  Leu  Tyr  Gly  Thr  Arg  Asn  Thr  Gln  Tyr
               5                              10
```

( 2 ) INFORMATION FOR SEQ ID NO:3:

( i ) SEQUENCE CHARACTERISTICS:
        ( A ) LENGTH: 12 amino acids
        ( B ) TYPE: amino acid
        ( D ) TOPOLOGY: linear ( x i ) SEQUENCE DESCRIPTION: SEQ ID NO:3:

```
Cys  Ala  Ser  Lys  Arg  Val  Ser  Asp  Asn  Gly  Gln  Tyr
```

(2) INFORMATION FOR SEQ ID NO:4:

(i) SEQUENCE CHARACTERISTICS:
        (A) LENGTH: 13 amino acids
        (B) TYPE: amino acid
        (D) TOPOLOGY: linear (xi) SEQUENCE DESCRIPTION: SEQ ID NO:4:

Cys Ala Ser Met Gly Leu Ala Gly Gln Gly Thr Gln Tyr
              5                       10

(2) INFORMATION FOR SEQ ID NO:5:

(i) SEQUENCE CHARACTERISTICS:
        (A) LENGTH: 12 amino acids
        (B) TYPE: amino acid
        (D) TOPOLOGY: linear (xi) SEQUENCE DESCRIPTION: SEQ ID NO:5:

Cys Ser Ala Ile Asp Arg Ala Ser Tyr Glu Gln Tyr
              5                    10

(2) INFORMATION FOR SEQ ID NO:6:

(i) SEQUENCE CHARACTERISTICS:
        (A) LENGTH: 11 amino acids
        (B) TYPE: amino acid
        (D) TOPOLOGY: linear (xi) SEQUENCE DESCRIPTION: SEQ ID NO:6:

Cys Ala Ser Ser Thr Gly Asn Thr Gly Ala Phe
              5                 10

(2) INFORMATION FOR SEQ ID NO:7:

(i) SEQUENCE CHARACTERISTICS:
        (A) LENGTH: 11 amino acids
        (B) TYPE: amino acid
        (D) TOPOLOGY: linear (xi) SEQUENCE DESCRIPTION: SEQ ID NO:7:

Cys Ala Ser Arg Leu Ala Ser Asn Gly Gln Phe
              5                 10

(2) INFORMATION FOR SEQ ID NO:8:

(i) SEQUENCE CHARACTERISTICS:
        (A) LENGTH: 14 amino acids
        (B) TYPE: amino acid
        (D) TOPOLOGY: linear (xi) SEQUENCE DESCRIPTION: SEQ ID NO:8:

Cys Ala Ser Ser Leu Val Thr Ser Gly Tyr Asn Gly Gln Phe
              5                    10

(2) INFORMATION FOR SEQ ID NO:9:

(i) SEQUENCE CHARACTERISTICS:
        (A) LENGTH: 14 amino acids
        (B) TYPE: amino acid
        (D) TOPOLOGY: linear (xi) SEQUENCE DESCRIPTION: SEQ ID NO:9:

Cys Ala Ser Ser Tyr Pro Thr Ala Gly Asn Gln Pro Gln His
              5                    10

(2) INFORMATION FOR SEQ ID NO:10:

(i) SEQUENCE CHARACTERISTICS:
      (A) LENGTH: 13 amino acids
      (B) TYPE: amino acid
      (D) TOPOLOGY: linear (xi) SEQUENCE DESCRIPTION: SEQ ID NO:10:

Cys Ala Ser Asn Pro Gly Gly Val Asn Thr Gly Ala Phe
              5                   10

(2) INFORMATION FOR SEQ ID NO:11:

(i) SEQUENCE CHARACTERISTICS:
      (A) LENGTH: 12 amino acids
      (B) TYPE: amino acid
      (D) TOPOLOGY: linear (xi) SEQUENCE DESCRIPTION: SEQ ID NO:11:

Cys Ala Ser Ser Pro Arg Gly Ala Tyr Thr Gln Tyr
              5                   10

(2) INFORMATION FOR SEQ ID NO:12:

(i) SEQUENCE CHARACTERISTICS:
      (A) LENGTH: 14 amino acids
      (B) TYPE: amino acid
      (D) TOPOLOGY: linear (xi) SEQUENCE DESCRIPTION: SEQ ID NO:12:

Cys Ala Ser Arg Ser Asp Arg Val Gly Asn Tyr Gly Tyr Thr
              5                   10

(2) INFORMATION FOR SEQ ID NO:13:

(i) SEQUENCE CHARACTERISTICS:
      (A) LENGTH: 13 amino acids
      (B) TYPE: amino acid
      (D) TOPOLOGY: linear (xi) SEQUENCE DESCRIPTION: SEQ ID NO:13:

Cys Ala Asn Leu Arg Ala Ala Thr Asn Gly Lys Leu Phe
              5                   10

(2) INFORMATION FOR SEQ ID NO:14:

(i) SEQUENCE CHARACTERISTICS:
      (A) LENGTH: 14 amino acids
      (B) TYPE: amino acid
      (D) TOPOLOGY: linear (xi) SEQUENCE DESCRIPTION: SEQ ID NO:14:

Cys Ala Ser Ser Gly Arg Gly Asp Asp Asn Gln Pro Gln His
              5                   10